United States Patent [19]

Okamoto

[11] Patent Number: 5,755,969
[45] Date of Patent: May 26, 1998

[54] MICROBE-REMOVING METHOD

[75] Inventor: Kengo Okamoto, Omiya, Japan

[73] Assignee: Mitsubishi Materials Corporation, Tokyo, Japan

[21] Appl. No.: 748,614

[22] Filed: Nov. 13, 1996

[30] Foreign Application Priority Data

Nov. 13, 1995 [JP] Japan ................... 7-293984

[51] Int. Cl.$^6$ ................................ C02F 1/28
[52] U.S. Cl. ................................ 210/691
[58] Field of Search ................... 210/690, 691, 210/502.1; 423/308, 309, 311; 502/400, 439

[56] References Cited

U.S. PATENT DOCUMENTS 5,227,147  7/1993  Yoshimura et al. ............ 423/308

*Primary Examiner*—Ivars Cintins
*Attorney, Agent, or Firm*—Oblon, Spivak, McClelland, Maier & Neustadt, P.C.

[57] ABSTRACT

A microbe-removing material is provided made of hydroxyapatite having a mean c-axis length of from 1 µm to 1000 µm, preferably from 5 pm to 200 µm, and an aspect ratio of 5 or more, preferably 10 or more, having good liquid permeability, while also having high microbe-adsorbing power and large adsorption capacity. The material can remove all microbes irrespective of their sizes and can adsorb and remove even acidic microbes.

10 Claims, No Drawings

5,755,969

MICROBE-REMOVING METHOD

FIELD OF THE INVENTION

The present invention relates to a microbe-removing material for removing bacteria and viruses in the food fermentation industry and in the cultivation and production of biochemical substances, and for removing bacteria and viruses from body fluids for medical use and from drinking water.

BACKGROUND OF THE INVENTION

Conventional microbe removing materials typically are porous inorganic substances, such as silica, activated charcoal and diatomaceous earth; non-woven fabrics or hollow organic fibers such as celluloses, polyethylenes and polyesters (see Japanese Patent Application Laid-Open Nos. 4-156933 and 6-63132); and fibrous metal substances, such as stainless steel, inconel, or hastelloy (see Japanese Patent Application Laid-Open No. 5-130858).

In addition, porous hydroxyapatite obtained from the hard tissue of vertebrates, and hydroxyapatite produced by wet processes have also been used as microbe removing materials.

Calcined hydroxyapatite prepared by calcining the above-mentioned hydroxyapatite at a temperature falling between 600° C. and 1400° C. has also been used as a microbe-removing material.

Conventional porous-type microbe-removing materials, such as those mentioned above, capture microbes in their pores to thereby remove them from the other substances.

However, these porous, inorganic substances can only adsorb microbes of sufficient sizes to be captured in the pores of the inorganic substances, but cannot capture the other microbes, which therefore pass through the inorganic substances together with the processed liquids.

In addition, the adsorption of microbes onto such porous, inorganic substances is not firm, since it is due to a merely bonding between them. Moreover, the adsorption capacity of the porous inorganic substances is small. For these reasons, the porous inorganic substances are not satisfactory for the removal of microbes to purify liquids.

On the other hand, in fibrous filters made of organic polymer fibers or made of metal, the meshes of the fibrous materials are used as sieves. Therefore, these fibrous filters can only physically fractionate and filter substances of different sizes.

The microbe-separating mechanism of hydroxyapatite is to attain ionizing adsorption, and is different from the physical adsorption to be attained by the above-mentioned, conventional microbe-separating materials. Therefore, hydroxyapatite has strong adsorption and separation characteristics specific to particular microbes. In addition, due to the stereospecific adsorbability of the adsorbing sites on its surface, hydroxyapatite is sensitive to the difference in the functional groups existing on the surfaces of microbes. For these reasons, hydroxyapatite is expected to have good adsorption and separation characteristics specific to the type of microbes.

However, the hydroxyapatite that has been used in conventional microbe-separating materials is extracted from natural organisms or is synthesized by wet processes. Hydroxyapatite of this type is poor in crystallinity and has poor adsorbability. In addition, it is in the form of fine submicron-sized particles. Therefore, it cannot be shaped into filters by itself. If it is used as a microbe-removing material, its liquid permeability cannot be ensured.

Calcined hydroxyapatite prepared by calcining wet-process synthesized hydroxyapatite at a temperature falling between 600° C. and 1400° C. may be used as a microbes-removing material. However, it cannot satisfactorily adsorb acidic biochemical substances, such as acidic microbes, since the growth of the A-plane of each particle's crystal structure is not acceptable.

SUMMARY OF THE INVENTION

Accordingly, one object of the present invention is to provide a microbe-removing material capable of removing microbes based on both size and ionic state.

A further object of the present invention is to provide a microbe-removing material that is sensitive to differences in the functional groups existing on the surfaces of microbes, and therefore can selectively remove different kinds of microbes.

These and further objects of the present invention have been satisfied by the discovery of a microbe-removing material comprising hydroxyapatite having a mean c-axis length of from 1 µm to 1000 µm and an aspect ratio of 5 or more.

DETAILED DESCRIPTION OF THE PREFERRED EMBODIMENTS

The present invention relates to a microbe-removing material comprising hydroxyapatite having a mean c-axis length of from 1 µm to 1000 µm, preferably from 5 µm to 200 µm and an aspect ratio of 5 or more, preferably of 10 or more.

Since they are synthesized by a hydrothermal reaction, the hydroxyapatite whiskers used as the microbe-removing material of the present invention have good crystallinity and liquid-permeability. In addition, since the structure of the adsorbing sites on the surfaces of the crystals is well ordered, the crystalline hydroxyapatite whiskers have high adsorbability with a large adsorption capacity and have good adsorption and separation characteristics.

Moreover, since the hydroxyapatite whiskers used in the present invention have A-planes that have been predominantly grown in the c-axis direction, they can remove not only microbes that can be adsorbed by the whiskers on their C-planes but also those that can be selectively adsorbed by them onto their A-planes.

Accordingly, the microbe-removing material of the present invention is sensitive to differences in the functional groups existing on the surfaces of microbes, and therefore can selectively remove different kinds of microbes.

While the ability of the microbe-removing material of the present invention to selectively remove specific microbes is not well understood and the present inventors do not wish to be bound by any particular theory regarding their mode of operation, it is believed that the ability of the microbe-removing material of the present invention to selectively remove specific microbes may be for the following reasons:

The hydroxyapatite, on which the present invention is based, is in the form of hexagonal pillar crystals having crystal planes with different properties, the A-plane corresponding to the side plane and the C-plane corresponding to the bottom plane.

The A-plane has adsorbing sites (C-sites) composed of positively-charged calcium ions, while the C-plane has adsorbing sites (P-sites) composed of negatively-charged phosphate ions.

Therefore, acidic biochemical substances having many carboxyl groups and phosphate groups should be adsorbed onto the C-sites, while basic biochemical substances having many amino groups should be adsorbed onto the P-sites. Such selectivity ensures selective removability of the microbes from the microbe-removing material of the invention.

In the present invention, the hydroxyapatite whiskers are preferably used in the form of layers or after having been shaped into filters of compacted hydroxyapatite whiskers.

In using the microbe-removing material of the present invention, all microbes which are larger than the pores of the material can be removed as residues, irrespective of the kind of microbes, while microbes that are smaller than the pores of the material are selectively adsorbed by the hydroxyapatite whiskers onto their adsorbing sites depending on the properties of the functional groups of the microbes.

The microbe-removing material provided by the present invention comprises hydroxyapatite having a mean c-axis length of from 1 µm to 1000 µm and an aspect ratio of 5 or more.

If the mean c-axis length is smaller than 1 µm, the material does not have good liquid permeability. If the mean c-axis is larger than 1000 µm, the meshes of the material are too large with the result that almost all microbes pass through. By requiring the aspect ratio of the hydroxyapatite of the present invention to be 5 or more, the adsorbability of the hydroxyapatite whiskers on their A-planes is increased, with higher aspect ratios providing further improvements in adsorbability on the A planes.

Preferably, the microbe-removing material of the present invention comprises hydroxyapatite having a mean c-axis length of from 5 µm to 200 µm and an aspect ratio of 10 or more.

The mean c-axis length of the hydroxyapatite of the present invention is preferably not smaller than 5 µm in order to ensure satisfactory liquid permeability of the material. The mean c-axis length is preferably not larger than 200 µm in order to reduce the number of microbes that pass through the large meshes due to a c-axis length larger than 200 µm.

The term "microbes" as used herein includes not only so-called bacteria but also other microorganisms, such as viruses, rickettsiae, chlamydiae, mycoplasmae, spirochaetae and fungi.

As mentioned above, the microbe-removing material of the present invention can be used by itself or after having been formed into layers or filters, to remove microbes. If desired, the material can be supported by any conventional support such as non-woven fabrics, cotton-like material of natural or synthetic organic fibers, cotton-like material of inorganic fibers, or filter cloth or paper made of such fibers.

Having generally described this invention, a further understanding can be obtained by reference to certain specific examples which are provided herein for purposes of illustration only and are not intended to be limiting unless otherwise specified.

EXAMPLES

Example 1

25 g of lactic acid and 6.89 g of 85% $H_3PO_4$ were dissolved in 500 ml of water, and 7.37 g of $Ca(OH)_2$ was added thereto. The resulting solution was subjected to hydrothermal treatment at 165° C. for 5 hours to prepare a synthetic hydroxyapatite.

The c-axis length and the aspect ratio of this hydroxyapatite were measured with an optical microscope, resulting in a mean c-axis length of 21 µm and a mean aspect ratio of 18.

Test liquids each containing $10^6$ cells/ml of *Escherichia coli*, *Staphylococcus aureus*, or influenza virus, separately, were prepared. 0.1 g of the powdery hydroxyapatite prepared above was added to 4 ml of each test liquid, and fully stirred. These test liquids were left stationary for 10 minutes, and the number of cells in the resulting supernatant of each test liquid was counted, from which the ability of the hydroxyapatite to adsorb the cells was determined.

As comparative examples, the following samples were tested in the same manner as above.

(1) 112 g of calcium hydroxide was suspended in 3 liters of water, and phosphoric acid was added dropwise thereto, while stirring, to attain a molar ratio of Ca/P of 1.67. The resulting hydroxyapatite slurry was dried, using a spray drier, into particles having a mean particle size of 15 µm and an aspect ratio of about 2.0. The wet-process hydroxyapatite thus synthesized was used as one comparative sample.

(2) The wet-process hydroxyapatite prepared above was calcined at 900° C. for 1 hour to prepare a calcined hydroxyapatite having a mean particle size of 12 µm and an aspect ratio of about 2.5. This was used as another comparative sample.

(3) A high-purity silica having a mean particle size of 12 µm was used as still another comparative sample.

(4) As a blank control, nothing was added to the test liquids.

The results for *Escherichia coli* are shown in Table 1; those for *Staphylococcus aureus* in Table 2; and those for influenza virus in Table 3.

From these data, the ability of the hydrothermal-process hydroxyapatite of the present invention to adsorb the cells can be seen to be the greatest.

TABLE 1

*Escherichia coli*

| Sample Tested | Number of Cells (/ml) |
| --- | --- |
| Hydrothermal-process Hydroxyapatite | $5.0 \times 10^3$ |
| Wet-process Hydroxyapatite | $3.0 \times 10^5$ |
| Calcined Hydroxyapatite | $7.0 \times 10^4$ |
| Silica | $3.0 \times 10^6$ |
| Blank | $5.0 \times 10^6$ |

TABLE 2

*Staphylococcus aureus*

| Sample Tested | Number of Cells (/ml) |
| --- | --- |
| Hydrothermal-process Hydroxyapatite | $2.0 \times 10^4$ |
| Wet-process Hydroxyapatite | $3.0 \times 10^6$ |
| Calcined Hydroxyapatite | $3.0 \times 10^5$ |
| Silica | $3.0 \times 10^6$ |
| Blank | $6.0 \times 10^6$ |

TABLE 3

Influenza Virus

| Sample Tested | Number of Cells (/ml) |
| --- | --- |
| Hydrothermal-process Hydroxyapatite | $7.0 \times 10^3$ |

TABLE 3-continued

Influenza Virus

| Sample Tested | Number of Cells (/ml) |
|---|---|
| Wet-process Hydroxyapatite | $4.0 \times 10^5$ |
| Calcined Hydroxyapatite | $8.0 \times 10^4$ |
| Silica | $2.0 \times 10^6$ |
| Blank | $7.0 \times 10^6$ |

Example 2

Three samples which are the same hydrothermal-process hydroxyapatite and calcined hydroxyapatite as those used in Example 1, and a cellulose filter-material having a filter pore size of 1 μm were tested. Cylindrical containers having a diameter of 8 mm and a length of 100 mm were separately filled with 10 g of each sample to prepare microbe-removing containers.

A test liquid containing $10^6$ cells/ml each of lactic acid bacteria (mean size: 5 μm), *Escherichia coli* (mean size: 2 μm), *Staphylococcus aureus* (mean size: 0.5 μm), mycoplasma (mean size: 0.2 μm) and influenza virus (mean size: 0.1 μm) was prepared. 10 ml of the test liquid was introduced into each microbe-removing container at a flow rate of 3 ml/min, and the number of the cells in the resulting filtrate that passed through each container was counted.

The data obtained are shown in Table 4.

Since the filtrates contained neither cells of lactic acid bacteria nor cells of *Escherichia coli*, the data for these were omitted in Table 4.

As in Table 4, the cellulose filter sample removed bacteria that were larger than the filter pore size but could not sufficiently remove the others smaller than the filter pore size.

As opposed to this, the hydroxyapatite of the present invention effectively removed all the tested microbes.

TABLE 4

| Sample Tested | *Staphylococcus aureus* | Mycoplasma | Influenza Virus |
|---|---|---|---|
| Hydrothermal-process Hydroxyapatite | $1.0 \times 10^2$ | $6.0 \times 10^2$ | $2.4 \times 10^3$ |
| Calcined Hydroxyapatite | $7.0 \times 10^3$ | $2.0 \times 10^4$ | $6.5 \times 10^4$ |
| Cellulose Filter | $1.0 \times 10^6$ | $1.0 \times 10^6$ | $1.0 \times 10^6$ |

The microbe-removing material of the present invention has good liquid permeability, high microbe-adsorbing power and large adsorption capacity. In addition, since it has a large area ratio of A-plane, the hydroxyapatite of the invention can efficiently adsorb and remove even acidic microbes.

This application is based on Japanese Patent Application Hei 7-293984, filed with the Japanese Patent Office on Nov. 13, 1995, the entire contents of which are hereby incorporated by reference.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for removal of microbes from a solution containing the same, comprising:

contacting the solution containing the microbes with a microbe-removing material comprising hydrothermic hydroxyapatite having a mean c-axis length of from 1 μm to 1000 μm and an aspect ratio of 5 or more.

2. The method as claimed in claim 1, wherein said contacting step is performed by passing the solution through a filter prepared from the microbe-removing material.

3. The method as claimed in claim 1, wherein said microbe-removing material comprises a hydrothermic hydroxyapatite having a mean c-axis length of from 5 μm to 200 μm.

4. The method as claimed in claim 1, wherein said microbe-removing material comprises a hydrothermic hydroxyapatite having an aspect ratio of 10 or more.

5. The method as claimed in claim 1, wherein said microbe-removing material comprises a hydrothermic hydroxyapatite having a mean c-axis length of from 5 μm to 200 μm and an aspect ratio of 10 or more.

6. The method as claimed in claim 1, wherein the microbes are selected from the group consisting of bacteria, viruses, rickettsiae, chlamydiae, mycoplasmae, spirochaetae, fungi and mixtures thereof.

7. The method as claimed in claim 1, wherein the microbes are either basic or acidic.

8. The method as claimed in claim 1, wherein the microbes have surface carboxyl or phosphate groups and are acidic.

9. The method as claimed in claim 1, wherein the microbes have surface amino groups and are basic.

10. A method for removing microbes from a solution comprising contacting the solution with hydrothermic hydroxyapatite having a mean c-axis length of from 1 μm to 1000 μm and an aspect ratio of 5 or more, wherein the microbes have a mean size of 0.1 μm to 2 μm.

* * * * *